United States Patent
Monahan et al.

(10) Patent No.: US 7,148,205 B2
(45) Date of Patent: *Dec. 12, 2006

(54) INTRAVASCULAR DELIVERY OF NON-VIRAL NUCLEIC ACID

(75) Inventors: Sean D. Monahan, Madison, WI (US); Jon A. Wolff, Madison, WI (US); Paul M. Slattum, Madison, WI (US); James E. Hagstrom, Middleton, WI (US); Vladimir G. Budker, Middleton, WI (US); David B. Rozema, Madison, WI (US)

(73) Assignee: Mirus Bio Corporation, Madison, WI (US)

( * ) Notice: Subject to any disclaimer, the term of this patent is extended or adjusted under 35 U.S.C. 154(b) by 528 days.

This patent is subject to a terminal disclaimer.

(21) Appl. No.: 10/600,290

(22) Filed: Jun. 20, 2003

(65) Prior Publication Data

US 2004/0019007 A1  Jan. 29, 2004

Related U.S. Application Data

(60) Division of application No. 09/447,966, filed on Nov. 23, 1999, now Pat. No. 6,627,616, which is a continuation-in-part of application No. 09/391,260, filed on Sep. 7, 1999, now abandoned, which is a division of application No. 08/975,573, filed on Nov. 21, 1997, now Pat. No. 6,265,387, which is a continuation of application No. 08/571,536, filed on Dec. 13, 1995, now abandoned.

(51) Int. Cl.
  *A61K 31/70*  (2006.01)
  *C07H 21/04*  (2006.01)
(52) U.S. Cl. .................. 514/44; 536/23.1; 536/24.5
(58) Field of Classification Search .................. None
  See application file for complete search history.

(56) References Cited

U.S. PATENT DOCUMENTS 6,627,616 B1 *  9/2003  Monahan et al. ............. 514/44

\* cited by examiner

*Primary Examiner*—Joseph Woitach
(74) *Attorney, Agent, or Firm*—Mark K. Johnson; Kirk Ekena

(57) ABSTRACT

Disclosed is a process for transfecting genetic material into a mammalian cell to alter endogenous properties of the cell. The process comprises designing a polynucleotide for transfection. Then the polynucleotide is inserted into a mammalian vessel such as a tail vein or artery. Prior to insertion, subsequent to insertion, or concurrent with insertion the permeability of the vessel is increased thereby the genetic material is delivered to the parenchymal cell altering endogenous properties of the cell.

14 Claims, 3 Drawing Sheets

SEQUENCE LISTING

<160> NUMBER OF SEQ ID NOS: 1

<210> SEQ ID NO 1
<211> LENGTH: 18
<212> TYPE: PRT
<213> ORGANISM: Artificial
<220> FEATURE:
<223> OTHER INFORMATION: synthetic peptide

<400> SEQUENCE: 1

Lys Leu Leu Lys Lys Leu Leu Lys Leu Trp Lys Lys Leu Leu Lys Lys
1               5                   10                  15

Leu Lys

INTRAVASCULAR DELIVERY OF NON-VIRAL NUCLEIC ACID

CROSS-REFERENCE TO RELATED APPLICATIONS

This application is a Divisional from non-provisional application U.S. Ser. No. 09/447,966, filed Nov. 23, 1999 now U.S. Pat. No. 6,627,616, which is a Continuation-In-Part from nonprovisional application Ser. No. 09/391,260, filed Sep. 7, 1999 now abandoned which is a Divisional from nonprovisional application Ser. No. 08/975,573 filed Nov. 21, 1997, issued as U.S. Pat. No. 6,265,387, which is a Continuation from Ser. No. 08/571,536, filed Dec. 13, 1995, abandoned.

FEDERALLY SPONSORED RESEARCH

N/A

FIELD OF THE INVENTION

The invention relates to compounds and methods for use in biologic systems. More particularly, processes that transfer nucleic acids into cells are provided. Nucleic acids in the form of naked DNA or a nucleic acid combined with another compound are delivered to cells.

BACKGROUND

Biotechnology includes the delivery of a genetic information to a cell to express an exogenous nucleotide sequence, to inhibit, eliminate, augment, or alter expression of an endogenous nucleotide sequence, or to express a specific physiological characteristic not naturally associated with the cell. Polynucleotides may be coded to express a whole or partial protein, or may be anti-sense.

A basic challenge for biotechnology and thus its subpart, gene therapy, is to develop approaches for delivering genetic information to cells of a patient in a way that is efficient and safe. This problem of "drug delivery," where the genetic material is a drug, is particularly challenging. If genetic material are appropriately delivered they can potentially enhance a patient's health and, in some instances, lead to a cure. Therefore, a primary focus of gene therapy is based on strategies for delivering genetic material in the form of nucleic acids. After delivery strategies are developed they may be sold commercially since they are then useful for developing drugs.

Delivery of a nucleic acid means to transfer a nucleic acid from a container outside a mammal to near or within the outer cell membrane of a cell in the mammal. The term transfection is used herein, in general, as a substitute for the term delivery, or, more specifically, the transfer of a nucleic acid from directly outside a cell membrane to within the cell membrane. The transferred (or transfected) nucleic acid may contain an expression cassette. If the nucleic acid is a primary RNA transcript that is processed into messenger RNA, a ribosome translates the messenger RNA to produce a protein within the cytoplasm. If the nucleic acid is a DNA, it enters the nucleus where it is transcribed into a messenger RNA that is transported into the cytoplasm where it is translated into a protein. Therefore if a nucleic acid expresses its cognate protein, then it must have entered a cell. A protein may subsequently be degraded into peptides, which may be presented to the immune system.

It was first observed that the in vivo injection of plasmid DNA into muscle enabled the expression of foreign genes in the muscle (Wolff, J A, Malone, R W, Williams, P, et al. Direct gene transfer into mouse muscle in vivo. *Science* 1990;247:1465–1468.). Since that report, several other studies have reported the ability for foreign gene expression following the direct injection of DNA into the parenchyma of other tissues. Naked DNA was expressed following its injection into cardiac muscle (Acsadi, G., Jiao, S., Jani, A., Duke, D., Williams, P., Chong, W., Wolff, J. A. Direct gene transfer and expression into rat heart in vivo. The New Biologist 3(1), 71–81, 1991.).

SUMMARY

In one preferred embodiment, a process is described for delivering a polynucleotide into a parenchymal cell of a mammal, comprising making a polynucleotide such as a nucleic acid. Then, inserting the polynucleotide into a mammalian vessel, such as a blood vessel and increasing the permeability of the vessel. Finally, delivering the polynucleotide to the parenchymal cell thereby altering endogenous properties of the cell. Increasing the permeability of the vessel consists of increasing pressure against vessel walls. Increasing the pressure consists of increasing a volume of fluid within the vessel. Increasing the volume consists of inserting the polynucleotide in a solution into the vessel wherein the solution contains a compound which complexes with the polynucleotide. A specific volume of the solution is inserted within a specific time period. Increased pressure is controlled by altering the specific volume of the solution in relation to the specific time period of insertion. The vessel may consist of a tail vein. The parenchymal cell is a cell selected from the group consisting of liver cells, spleen cells, heart cells, kidney cells and lung cells.

In another embodiment, a process is described for delivering a polynucleotide complexed with a compound into a parenchymal cell of a mammal, comprising making the polynucleotide-compound complex wherein the compound is selected from the group consisting of amphipathic compounds, polymers and non-viral vectors. Inserting the polynucleotide into a mammalian vessel and increasing the permeability of the vessel. Then, delivering the polynucleotide to the parenchymal cell thereby altering endogenous properties of the cell.

In yet another embodiment, a process is described for transfecting genetic material into a mammalian cell, comprising designing the genetic material for transfection. Inserting the genetic material into a mammalian blood vessel. Increasing permeability of the blood vessel and delivering the genetic material to the parenchymal cell for the purpose of altering endogenous properties of the cell.

DETAILED DESCRIPTION

Figure 1:
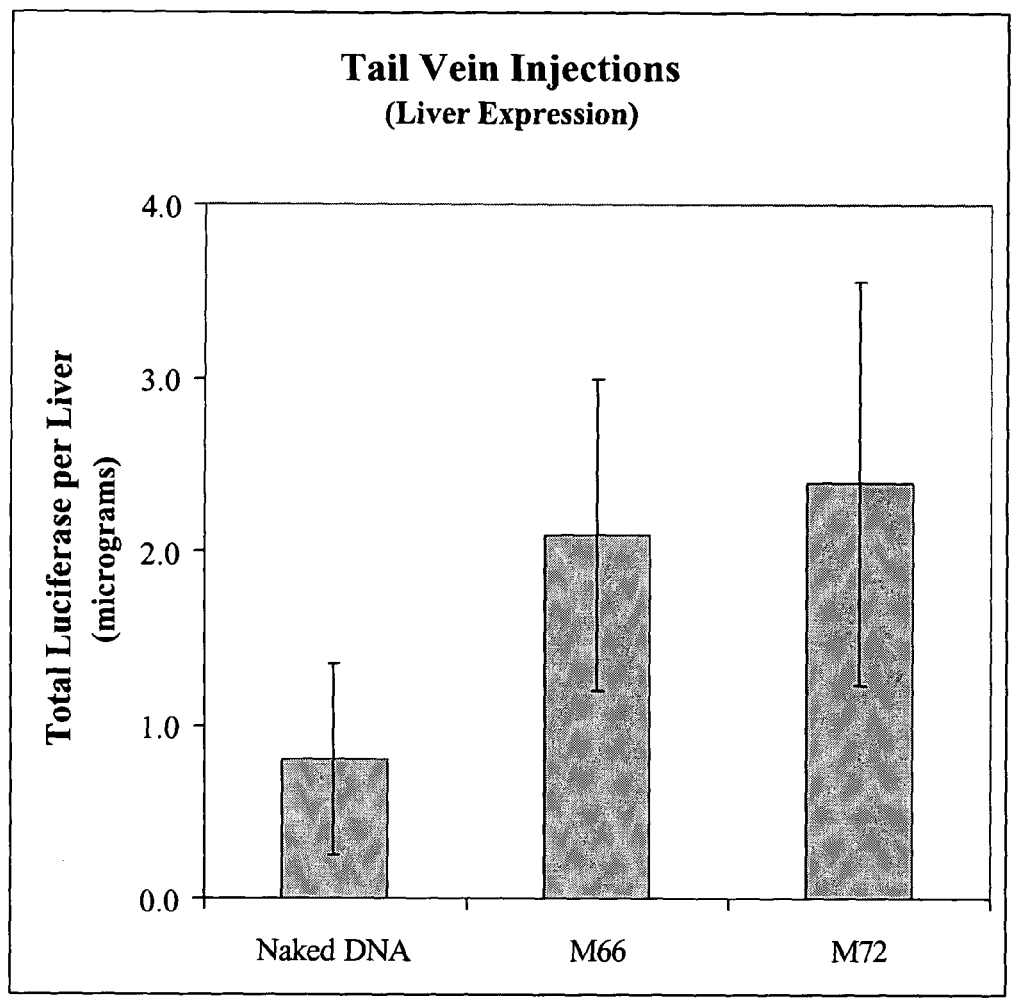
FIG. 1 illustrates high level luciferase expression in liver following tail vein injections.

We have found that an intravascular route of administration allows a polynucleotide to be delivered to a parenchymal cell in a more even distribution than direct parenchymal injections. The efficiency of polynucleotide delivery and expression is increased by increasing the permeability of the tissue's blood vessel. Permeability is increased by increasing the intravascular hydrostatic (physical) pressure, delivering the injection fluid rapidly (injecting the injection fluid rapidly), using a large injection volume, and increasing permeability of the vessel wall. Expression of a foreign DNA is obtained in large number of mammalian organs including; liver, spleen, lung, kidney and heart by injecting the naked polynucleotide. Increased expression occurs when polynucleotide is mixed with another compound.

In a first embodiment the compound consists of an amphipathic compound. Amphipathic compounds have both hydrophilic (water-soluble) and hydrophobic (water-insoluble) parts. The amphipathic compound can be cationic or incorporated into a liposome that is positively-charged (cationic) or non-cationic which means neutral, or negatively-charged (anionic). In another embodiment the compound consists of a polymer. In yet another embodiment the compound consists of a non-viral vector. In one embodiment, the compound does not aid the transfection process in vitro of cells in culture but does aid the delivery process in vivo in the whole organism. We also show that foreign gene expression can be achieved in hepatocytes following the rapid injection of naked plasmid DNA in a large volume of physiologic solutions.

The term intravascular refers to an intravascular route of administration that enables a polymer, oligonucleotide, or polynucleotide to be delivered to cells more evenly distributed than direct injections. Intravascular herein means within an internal tubular structure called a vessel that is connected to a tissue or organ within the body of an animal, including mammals. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein.

Afferent blood vessels of organs are defined as vessels in which blood flows toward the organ or tissue under normal physiologic conditions. Efferent blood vessels are defined as vessels in which blood flows away from the organ or tissue under normal physiologic conditions. In the heart, afferent vessels are known as coronary arteries, while efferent vessels are referred to as coronary veins.

The term naked nucleic acids indicates that the nucleic acids are not associated with a transfection reagent or other delivery vehicle that is required for the nucleic acid to be delivered to a target cell. A transfection reagent is a compound or compounds used in the prior art that mediates nucleic acids entry into cells.

Parenchymal Cells

Parenchymal cells are the distinguishing cells of a gland or organ contained in and supported by the connective tissue framework. The parenchymal cells typically perform a function that is unique to the particular organ. The term "parenchymal" often excludes cells that are common to many organs and tissues such as fibroblasts and endothelial cells within blood vessels.

In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to an hepatic sinusoid and opposed sides to a bile canaliculus. Liver cells that are not parenchymal cells include cells within the blood vessels such as the endothelial cells or fibroblast cells. In one preferred embodiment hepatocytes are targeted by injecting the polynucleotide within the tail vein of a rodent such as a mouse.

In striated muscle, the parenchymal cells include myoblasts, satellite cells, myotubules, and myofibers. In cardiac muscle, the parenchymal cells include the myocardium also known as cardiac muscle fibers or cardiac muscle cells and the cells of the impulse connecting system such as those that constitute the sinoatrial node, atrioventricular node, and atrioventricular bundle. In one preferred embodiment striated muscle such as skeletal muscle or cardiac muscle is targeted by injecting the polynucleotide into the blood vessel supplying the tissue. In skeletal muscle an artery is the delivery vessel; in cardiac muscle, an artery or vein is used.

Polymers

A polymer is a molecule built up by repetitive bonding together of smaller units called monomers. In this application the term polymer includes both oligomers which have two to about 80 monomers and polymers having more than 80 monomers. The polymer can be linear, branched network, star, comb, or ladder types of polymer. The polymer can be a homopolymer in which a single monomer is used or can be copolymer in which two or more monomers are used. Types of copolymers include alternating, random, block and graft.

One of our several methods of nucleic acid delivery to cells is the use of nucleic acid-polycations complexes. It was shown that cationic proteins like histones and protamines or synthetic polymers like polylysine, polyarginine, polyornithine, DEAE dextran, polybrene, and polyethylenimine are effective intracellular delivery agents while small polycations like spermine are ineffective.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule that contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains two or more negative charges. The term polyion includes polycation, polyanion, zwitterionic polymers, and neutral polymers. The term zwitterionic refers to the product (salt) of the reaction between an acidic group and a basic group that are part of the same molecule. Salts are ionic compounds that dissociate into cations and anions when dissolved in solution. Salts increase the ionic strength of a solution, and consequently decrease interactions between nucleic acids with other cations.

In one embodiment, polycations are mixed with polynucleotides for intravascular delivery to a cell. Polycations provide the advantage of allowing attachment of DNA to the target cell surface. The polymer forms a cross-bridge between the polyanionic nucleic acids and the polyanionic surfaces of the cells. As a result the main mechanism of DNA translocation to the intracellular space might be non-specific adsorptive endocytosis which may be more effective then liquid endocytosis or receptor-mediated endocytosis.

Furthermore, polycations are a very convenient linker for attaching specific receptors to DNA and as result, DNA-polycation complexes can be targeted to specific cell types.

Additionally, polycations protect DNA in complexes against nuclease degradation. This is important for both extra- and intracellular preservation of DNA. The endocytic step in the intracellular uptake of DNA-polycation complexes is suggested by results in which DNA expression is only obtained by incorporating a mild hypertonic lysis step (either glycerol or DMSO). Gene expression is also enabled or increased by preventing endosome acidification with $NH_4Cl$ or chloroquine. Polyethylenimine which facilitates gene expression without additional treatments probably disrupts endosomal function itself. Disruption of endosomal function has also been accomplished by linking the polycation to endosomal-disruptive agents such as fusion peptides or adenoviruses.

Polycations also cause DNA condensation. The volume which one DNA molecule occupies in complex with polycations is drastically lower than the volume of a free DNA molecule. The size of DNA/polymer complex may be important for gene delivery in vivo. In terms of intravenous injection, DNA needs to cross the endothelial barrier and reach the parenchymal cells of interest.

The average diameter of liver fenestrae (holes in the endothelial barrier) is about 100 nm, increases in pressure and/or permeability can increase the size of the fenestrae. The fenestrae size in other organs is usually less. The size of the DNA complexes is also important for the cellular uptake process. DNA complexes should be smaller than 200 nm in at least one dimension. After binding to the target cells the DNA- polycation complex is expected to be taken up by endocytosis.

Polymers may incorporate compounds that increase their utility. These groups can be incorporated into monomers prior to polymer formation or attached to the polymer after its formation. The gene transfer enhancing signal (Signal) is defined in this specification as a molecule that modifies the nucleic acid complex and can direct it to a cell location (such as tissue cells) or location in a cell (such as the nucleus) either in culture or in a whole organism. By modifying the cellular or tissue location of the foreign gene, the expression of the foreign gene can be enhanced.

The gene transfer enhancing signal can be a protein, peptide, lipid, steroid, sugar, carbohydrate, nucleic acid or synthetic compound. The gene transfer enhancing signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1 and the ER-retaining signal (KDEL sequence), viral components such as influenza virus hemagglutinin subunit HA-2 peptides and other types of amphipathic peptides.

Cellular receptor signals are any signal that enhances the association of the gene with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asialoglycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

Polynucleotides

The term nucleic acid is a term of art that refers to a string of at least two base-sugar-phosphate combinations. (A polynucleotide is distinguished from an oligonucleotide by containing more than 120 monomeric units.) Nucleotides are the monomeric units of nucleic acid polymers. The term includes deoxyribonucleic acid (DNA) and ribonucleic acid (RNA) in the form of an oligonucleotide messenger RNA, anti-sense, plasmid DNA, parts of a plasmid DNA or genetic material derived from a virus. Anti-sense is a polynucleotide that interferes with the function of DNA and/or RNA. The term nucleic acids- refers to a string of at least two base-sugar-phosphate combinations. Natural nucleic acids have a phosphate backbone, artificial nucleic acids may contain other types of backbones, but contain the same bases. Nucleotides are the monomeric units of nucleic acid polymers. The term includes deoxyribonucleic acid (DNA) and ribonucleic acid (RNA). RNA may be in the form of an tRNA (transfer RNA), snRNA (small nuclear RNA), rRNA (ribosomal RNA), mRNA (messenger RNA), anti-sense RNA, and ribozymes. DNA may be in form plasmid DNA, viral DNA, linear DNA, or chromosomal DNA or derivatives of these groups. In addition these forms of DNA and RNA may be single, double, triple, or quadruple stranded. The term also includes PNAs (peptide nucleic acids), phosphorothioates, and other variants of the phosphate backbone of native nucleic acids.

A polynucleotide can be delivered to a cell to express an exogenous nucleotide sequence, to inhibit, eliminate, augment, or alter expression of an endogenous nucleotide sequence, or to express a specific physiological characteristic not naturally associated with the cell. Polynucleotides may be coded to express a whole or partial protein, or may be anti-sense.

A delivered polynucleotide can stay within the cytoplasm or nucleus apart from the endogenous genetic material. Alternatively, the polymer could recombine (become a part of) the endogenous genetic material. For example, DNA can insert into chromosomal DNA by either homologous or non-homologous recombination.

Vectors are polynucleic molecules originating from a virus, a plasmid, or the cell of a higher organism into which another nucleic fragment of appropriate size can be integrated without loss of the vectors capacity for self- replication; vectors typically introduce foreign DNA into host cells, where it can be reproduced. Examples are plasmids, cosmids, and yeast artificial chromosomes; vectors are often recombinant molecules containing DNA sequences from several sources. A vector includes a viral vector: for example, adenovirus; DNA; adenoassociated viral vectors (AAV) which are derived from adenoassociated viruses and are smaller than adenoviruses; and retrovirus (any virus in the family Retroviridae that has RNA as its nucleic acid and uses the enzyme reverse transcriptase to copy its genome into the DNA of the host cell's chromosome; examples include VSV G and retroviruses that contain components of lentivirus including HIV type viruses).

A non-viral vector is defined as a vector that is not assembled within an eukaryotic cell.

Permeability

In another preferred embodiment, the permeability of the vessel is increased. Efficiency of polynucleotide delivery and expression was increased by increasing the permeability of a blood vessel within the target tissue. Permeability is defined here as the propensity for macromolecules such as polynucleotides to move through vessel walls and enter the extravascular space. One measure of permeability is the rate at which macromolecules move through the vessel wall and out of the vessel. Another measure of permeability is the lack of force that resists the movement of polynucleotides being delivered to leave the intravascular space.

To obstruct, in this specification, is to block or inhibit inflow or outflow of blood in a vessel. Rapid injection may be combined with obstructing the outflow to increase permeability. For example, an afferent vessel supplying an organ is rapidly injected and the efferent vessel draining the tissue is ligated transiently. The efferent vessel (also called the venous outflow or tract) draining outflow from the tissue is also partially or totally clamped for a period of time sufficient to allow delivery of a polynucleotide. In the reverse, an efferent is injected and an afferent vessel is occluded.

In another preferred embodiment, the intravascular pressure of a blood vessel is increased by increasing the osmotic pressure within the blood vessel. Typically, hypertonic solutions containing salts such as NaCl, sugars or polyols such as mannitol are used. Hypertonic means that the osmolarity of the injection solution is greater than physiologic osmolarity. Isotonic means that the osmolarity of the injection solution is the same as the physiological osmolarity (the tonicity or osmotic pressure of the solution is similar to that of blood). Hypertonic solutions have increased tonicity and osmotic pressure similar to the osmotic pressure of blood and cause cells to shrink.

In another preferred embodiment, the permeability of the blood vessel can also be increased by a biologically-active molecule. A biologically-active molecule is a protein or a simple chemical such as papaverine or histamine that increases the permeability of the vessel by causing a change in function, activity, or shape of cells within the vessel wall such as the endothelial or smooth muscle cells. Typically, biologically-active molecules interact with a specific receptor or enzyme or protein within the vascular cell to change the vessel's permeability. Biologically-active molecules include vascular permeability factor (VPF) which is also known as vascular endothelial growth factor (VEGF). Another type of biologically-active molecule can also increase permeability by changing the extracellular connective material. For example, an enzyme could digest the extracellular material and increase the number and size of the holes of the connective material.

In another embodiment a non-viral vector along with a polynucleotide is intravascularly injected in a large injection volume. The injection volume is dependent on the size of the animal to be injected and can be from 1.0 to 3.0 ml or greater for small animals (i.e. tail vein injections into mice). The injection volume for rats can be from 6 to 35 ml or greater. The injection volume for primates can be 70 to 200 ml or greater. The injection volumes in terms of ml/body weight can be 0.03 ml/g to 0.1 ml/g or greater.

The injection volume can also be related to the target tissue. For example, delivery of a non-viral vector with a polynucleotide to a limb can be aided by injecting a volume greater than 5 ml per rat limb or greater than 70 ml for a primate. The injection volumes in terms of ml/limb muscle are usually within the range of 0.6 to 1.8 ml/g of muscle but can be greater. In another example, delivery of a polynucleotide to liver in mice can be aided by injecting the non-viral vector—polynucleotide in an injection volume from 0.6 to 1.8 ml/g of liver or greater. In another preferred embodiment, delivering a polynucleotide—non-viral vector to a limb of a primate (rhesus monkey), the complex can be in an injection volume from 0.6 to 1.8 ml/g of limb muscle or anywhere within this range.

In another embodiment the injection fluid is injected into a vessel rapidly. The speed of the injection is partially dependent on the volume to be injected, the size of the vessel to be injected into, and the size of the animal. In one embodiment the total injection volume (1–3 mls) can be injected from 15 to 5 seconds into the vascular system of mice. In another embodiment the total injection volume (6–35 mls) can be injected into the vascular system of rats from 20 to 7 seconds. In another embodiment the total injection volume (80–200 mls) can be injected into the vascular system of monkeys from 120 seconds or less.

In another embodiment a large injection volume is used and the rate of injection is varied. Injection rates of less than 0.012 ml per gram (animal weight) per second are used in this embodiment. In another embodiment injection rates of less than ml per gram (target tissue weight) per second are used for gene delivery to target organs. In another embodiment injection rates of less than 0.06 ml per gram (target tissue weight) per second are used for gene delivery into limb muscle and other muscles of primates.

Reporter Molecules

There are three types of reporter (marker) gene products that are expressed from reporter genes. The reporter gene/protein systems include:

a) Intracellular gene products such as luciferase, β-galactosidase, or chloramphenicol acetyl transferase. Typically, they are enzymes whose enzymatic activity can be easily measured.

b) Intracellular gene products such as β-galactosidase or green fluorescent protein which identify cells expressing the reporter gene. On the basis of the intensity of cellular staining, these reporter gene products also yield qualitative information concerning the amount of foreign protein produced per cell.

c) Secreted gene products such as growth hormone, factor IX, or alpha1-antitrypsin are useful for determining the amount of a secreted protein that a gene transfer procedure can produce. The reporter gene product can be assayed in a small amount of blood.

We have disclosed gene expression achieved from reporter genes in parenchymal cells. The terms "delivery," "delivering genetic information," "therapeutic" and "therapeutic results" are defined in this application as representing levels of genetic products, including reporter (marker) gene products, which indicate a reasonable expectation of genetic expression using similar compounds (nucleic acids), at levels considered sufficient by a person having ordinary skill in the art of delivery and gene therapy. For example: Hemophilia A and B are caused by deficiencies of the X-linked clotting factors VIII and IX, respectively. Their clinical course is greatly influenced by the percentage of normal serum levels of factor VIII or IX:<2%, severe; 2–5%, moderate; and 5–30% mild. This indicates that in severe patients only 2% of the normal level can be considered therapeutic. Levels greater than 6% prevent spontaneous bleeds but not those secondary to surgery or injury. A person having ordinary skill in the art of gene therapy would reasonably anticipate therapeutic levels of expression of a gene specific for a disease based upon sufficient levels of marker gene results. In the Hemophilia example, if marker genes were expressed to yield a protein at a level comparable in volume to 2% of the normal level of factor VIII, it can be reasonably expected that the gene coding for factor VIII would also be expressed at similar levels.

EXAMPLES

Enhanced Delivery of Naked DNA

Enhancement of in vivo Gene Expression by M-methyl-L-arginine (L-NMMA) Following Intravascular Delivery of Naked DNA:

Intravascular delivery of pCILuc via the iliac artery of rat following a short pre-treatment with L-NMMA delivery enhancer. A 4 cm long abdominal midline excision was performed in 150–200 g, adult Sprague-Dawley rats anesthesized with 80 mg/mg ketamine and 40 mg/kg xylazine. Microvessel clips were placed on external iliac, caudal epigastric, internal iliac and deferent duct arteries and veins to block both outflow and inflow of the blood to the leg. 3 ml of normal saline with 0.66 mM L-NMMA were injected into the external iliac artery. After 2 min 27 g butterfly needle was inserted into the external iliac artery and 10 ml of DNA solution (50 ug/ml pCILuc) in normal saline was injected within 8–9 sec. Luciferase assays was performed 2 days after injection on limb muscle samples (quadriceps femoris).

Organ Treatment Total Luciferase (Nanograms)
Muscle (quadriceps)+papaverine 9,999
Muscle (quadriceps)+0.66 mM L-NMMA 15,398
Muscle (quadriceps)+papaverine, +0.66 mM L-NMMA 24,829

2) Enhancement of in vivo Gene Expression by aurintricarboxylic Acid (ATA) Delivery Enhancer Following Intravascular Delivery of Naked DNA.

Intravascular delivery of pCILuc in the absence or presence of aurintricarboxylic acid via tail vein injection into mice. 10 micrograms of pCILuc was diluted to 2.5 ml with Ringers solution and aurintricarboxylic acid was added to a final concentration of 0.11 mg/ml. The DNA solution was injected into the tail vein of 25 g ICR mice with an injection time of ~7 seconds. Mice were sacrificed 24 hours after injection and various organs were assayed for luciferase expression.

Organ Treatment Total Relative Light Units per Organ
Liver none 55,300,000,000
Liver+ATA 109,000,000,000
Spleen none 63,200,000
Spleen+ATA 220,000,000
Lung none 100,000,000
Lung+ATA 128,000,000
Heart none 36,700,000
Heart+ATA 32,500,000
Kidney none 15,800,000
Kidney+ATA 82,400,000

DNA/Polymer Delivery

Rapid injection of pDNA/cationic polymer complexes (containing 10 μg of pCILuc; a luciferase expression vector utilizing the human CMV promoter) in 2.5 ml of Ringers solution (147 mM NaCl, 4 mM KCl, 1.13 mM CaCl2) into the tail vein of ICR mice facilitated expression levels higher than comparable injections using naked plasmid DNA (pCI-Luc). Maximal luciferase expression using the tail vein approach was achieved when the DNA solution was injected within 7 seconds. Luciferase expression was also critically dependent on the total injection volume and high level gene expression in mice was obtained following tail vein injection of polynucleotide/polymer complexes of 1, 1.5, 2, 2.5, and 3 ml total volume. There is a positive correlation between injection volume and gene expression for total injection volumes over 1 ml. For the highest expression efficiencies an injection delivery rate of greater than 0.003 ml per gram (animal weight) per second is likely required. Injection rates of 0.004, 0.006, 0.009, 0.012 ml per gram (animal weight) per second yield successively greater gene expression levels.

FIG. 1 above illustrates high level luciferase expression in liver following tail vein injections of naked plasmid DNA and plasmid DNA complexed with labile disulfide containing polycations L-cystine—1,4-bis(3-aminopropyl)piperazine copolymer (M66) and 5,5'-Dithiobis(2-nitrobenzoic acid)—Pentaethylenehexamine Copolymer (M72). The labile polycations were complexed with DNA at a 3:1 wt:wt ratio resulting in a positively charged complex. Complexes were injected into 25 gram ICR mice in a total volume of 2.5 ml of ringers solution.

Figure 2:
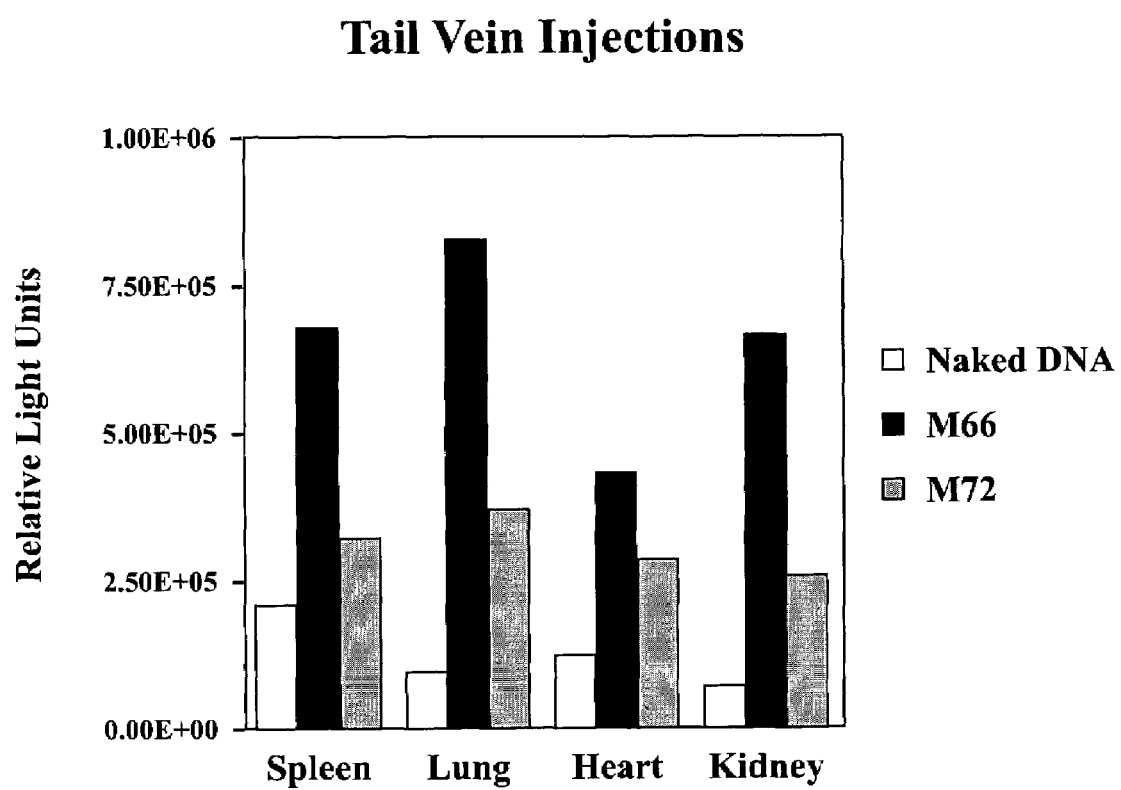
FIG. 2 indicates high level luciferase expression in spleen, lung, heart and kidney following tail vein injections.

FIG. 2 indicates high level luciferase expression in spleen, lung, heart and kidney following tail vein injections of naked plasmid DNA and plasmid DNA complexed with labile disulfide containing polycations M66 and M72. The labile polycations were complexed with DNA at a 3:1 wt:wt ratio resulting in a positively charged complex. Complexes were injected into 25 gram ICR mice in a total volume of 2.5 ml of ringers solution.

Luciferase Expression in a Variety of Tissues Following a Single Tail Vein Injection of pCILuc/66 Complexes:

DNA and polymer 66 were mixed at a 1:1.7 wt:wt ratio in water and diluted to 2.5 ml with Ringers solution as described. Complexes were injected into tail vein of 25 g ICR mice within 7 seconds. Mice were sacrificed 24 hours after injection and various organs were assayed for luciferase expression.

Organ Total Relative Light Units
Prostate 637,000
Skin (abdominal wall) 194,000
Testis 589,000
Skeletal Muscle (quadriceps) 35,000
fat (peritoneal cavity) 44,700
bladder 17,000
brain 247,000
pancreas 2,520,000

Directed Intravascular Injection of pCILuc/66 Polymer Complexes into Dorsal Vein of Penis Results in High Level Gene Expression in the Prostate and other Localized Tissues:

Complexes were formed as described for example above and injected rapidly into the dorsal vein of the penis (within 7 seconds). For directed delivery to the prostate with increased hydrostatic pressure, clamps were applied to the inferior vena cava and the anastomotic veins just prior to the injection and removed just after the injection (within 5–10 seconds). Mice were sacrificed 24 hours after injection and various organs were assayed for luciferase expression.

Organ Total Relative Light Units per Organ
Prostate 129,982,450
Testis 4,229,000
fat (around bladder) 730,300
bladder 618,000

Intravascular Tail Vein Injection into Rat Results in High Level Gene Expression in a Variety of Organs:

100 micrograms of pCILuc was diluted into 30 mls Ringers solution and injected into the tail vein of 480 gram Harlan Sprague Dawley rat. The entire volume was delivered within 15 seconds. 24 hours after injection various organs were harvested and assayed for luciferase expression.

Organ Total Relative Light Units per Organ
Liver 30,200,000,000
Spleen 14,800,000
Lung 23,600,000
Heart 5,540,000
Kidney 19,700,000
Prostate 3,490,000
Skeletal Muscle (quadriceps) 7,670,000

Cleavable Polymers

A prerequisite for gene expression is that once DNA/cationic polymer complexes have entered a cell the polynucleotide must be able to dissociate from the cationic polymer. This may occur within cytoplasmic vesicles (i.e. endosomes), in the cytoplasm, or the nucleus. We have developed bulk polymers prepared from disulfide bond containing co-monomers and cationic co-monomers to better facilitate this process. These polymers have been shown to condense polynucleotides, and to release the nucleotides after reduction of the disulfide bond. These polymers can be used to effectively complex with DNA and can also protect DNA from DNases during intravascular delivery to the liver and other organs. After internalization into the cells the polymers are reduced to monomers, effectively releasing the DNA, as a result of the stronger reducing conditions (glutathione) found in the cell. Negatively charged polymers can be fashioned in a similar manner, allowing the condensed nucleic acid particle (DNA+polycation) to be "recharged" with a cleavable anionic polymer resulting in a particle with a net negative charge that after reduction of disulfide bonds will release the polynucleic acid. The reduction potential of the disulfide bond in the reducible co-monomer can be adjusted by chemically altering the disulfide bonds environment. This will allow the construction of particles whose release characteristics can be tailored so that the polynucleic acid is released at the proper point in the delivery process.

Cleavable Cationic Polymers

Cationic cleavable polymers are designed such that the reducibility of disulfide bonds, the charge density of polymer, and the functionalization of the final polymer can all be controlled. The disulfide co-monomer can have reactive ends chosen from, but not limited to the following: the disulfide compounds contain reactive groups that can undergo acylation or alkylation reactions. Such reactive groups include isothiocyanate, isocyanate, acyl azide, N-hydroxysuccinimide esters, succinimide esters, sulfonyl chloride, aldehyde, epoxide, carbonate, imidoester, carboxylate, alkylphosphate, arylhalides (e.g. difluoro-dinitrobenzene) or succinic anhydride.

If functional group A (cationic co-monomer) is an amine then B (disulfide containing comonomer) can be (but not restricted to) an isothiocyanate, isocyanate, acyl azide, N-hydroxysuccinimide, sulfonyl chloride, aldehyde (including formaldehyde and glutaraldehyde), epoxide, carbonate, imidoester, carboxylate, or alkylphosphate, arylhalides (difluoro-dinitrobenzene) or succinic anhyride. In other terms when function A is an amine then function B can be acylating or alkylating agent.

If functional group A is a sulfhydryl then functional group B can be (but not restricted to) an iodoacetyl derivative, maleimide, vinyl sulfone, aziridine derivative, acryloyl derivative, fluorobenzene derivatives, or disulfide derivative (such as a pyridyl disulfide or 5-thio-2-nitrobenzoic acid{TNB} derivatives).

If functional group A is carboxylate then functional group B can be (but not restricted to) a diazoacetate or an amine, alcohol, or sulfhydryl in which carbonyldiimidazole or carbodiimide is used.

If functional group A is an hydroxyl then functional group B can be (but not restricted to) an epoxide, oxirane, or an carboxyl group in which carbonylduimidazole or carbodiimide or N, N'-disuccinimidyl carbonate, or N-hydroxysuccinimidyl chloroformate is used.

If functional group A is an aldehyde or ketone then function B can be (but not restricted to) an hydrazine, hydrazide derivative, a mine (to form a Schiff Base that may or may not be reduced by reducing agents such as NaCNBH$_3$).

The polymer is formed by simply mixing the cationic, and disulfide-containing co-monomers under appropriate conditions for reaction. The resulting polymer may be purified by dialysis or size-exclusion chromatography.

The reduction potential of the disulfide bond can be controlled in two ways. Either by altering the reduction potential of the disulfide bond in the disulfide-containing co-monomer, or by altering the chemical environment of the disulfide bond in the bulk polymer through choice the of cationic co-monomer.

The reduction potential of the disulfide bond in the co-monomer can be controlled by synthesizing new cross-linking reagents. Dimethyl 3,3'-dithiobispropionimidate (DTBP) is a commercially available disulfide containing crosslinker from Pierce Chemical Co. This disulfide bond is reduced by dithiothreitol (DTT), but is only slowly reduced, if at all by biological reducing agents such as glutathione. More readily reducible crosslinkers have been synthesized by Mirus. These crosslinking reagents are based on aromatic disulfides such as 5,5'-dithiobis(2-nitrobenzoic acid) and 2,2'-dithiosalicylic acid. The aromatic rings activate the disulfide bond towards reduction through delocalization of the transient negative charge on the sulfur atom during reduction. The nitro groups further activate the compound to reduction through electron withdrawal which also stabilizes the resulting negative charge.

Cleavable disulfide containing co-monomers:
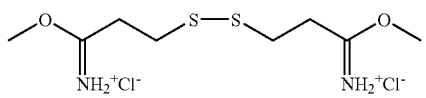
DTBP
Activated Disulfide Crosslinkers
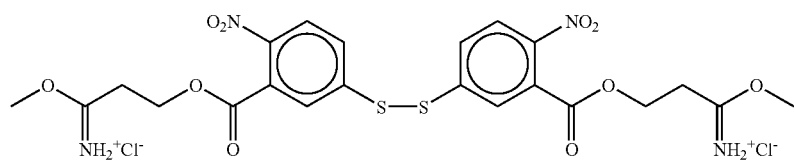
diimidate activated crosslinker
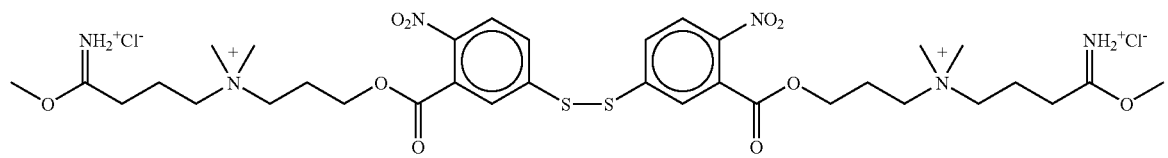
diimidate activated crosslinker with additional positive charge
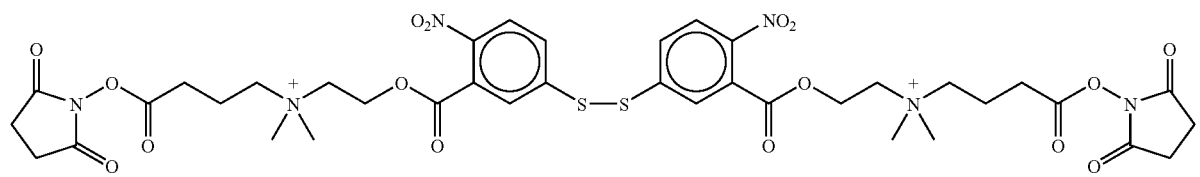
di-NHS ester activated crosslinker with additional positive charge
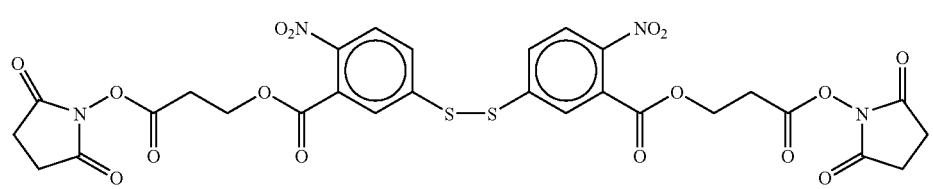

di-NHS ester activated crosslinker with no additional positive charge

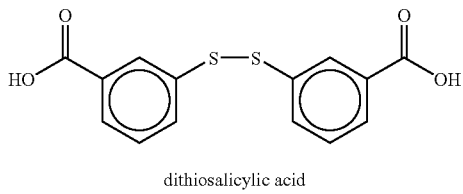

dithiosalicylic acid

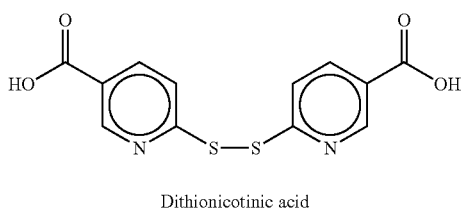

Dithionicotinic acid

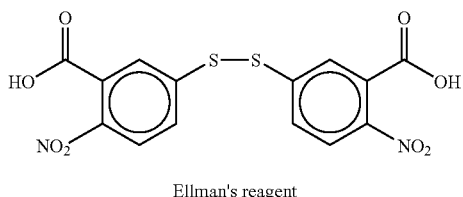

Ellman's reagent

The reduction potential can also be altered by proper choice of cationic co-monomer. For example when DTBP is polymerized along with diaminobutane the disulfide bond is reduced by DTT, but not glutathione. When ethylenediamine is polymerized with DTBP the disulfide bond is now reduced by glutathione. This is apparently due to the proximity of the disulfide bond to the amidine functionality in the bulk polymer.

The charge denisty of the bulk polymer can be controlled through choice of cationic monomer, or by incorporating positive charge into the disulfide co-monomer. For example spermine a molecule containing 4 amino groups spaced by 3-4-3 methylene groups could be used for the cationic monomer. Because of the spacing of the amino groups they would all bear positive charges in the bulk polymer with the exception of the end primary amino groups that would be derivitized during the polymerization. Another monomer that could be used is N,N'-bis(2-aminoethyl)-1,3-propediamine (AEPD) a molecule containing 4 amino groups spaced by 2-3-2 methylene groups. In this molecule the spacing of the amines would lead to less positive charge at physiological pH, however the molecule would exhibit pH sensitivity, that is bear different net positive charge, at different pH's. A molecule such as tetraethylenepentamine could also be used as the cationic monomer, this molecule consists of 5 amino groups each spaced by two methylene units. This molecule would give the bulk polymer pH sensitivity, due to the spacing of the amino groups as well as charge density, due to the number and spacing of the amino groups. The charge density can also be affected by incorporating positive charge into the disulfide containing monomer, or by using imidate groups as the reactive portions of the disulfide containing monomer as imidates are transformed into amidines upon reaction with amine which retain the positive charge.

The bulk polymer can be designed to allow further functionalization of the polymer by incorporating monomers with protected primary amino groups. These protected primary amines can then be deprotected and used to attach other functionalities such as nuclear localizing signals, endosome disrupting peptides, cell-specific ligands, fluorescent marker molecules, as a site of attachment for further crosslinking of the polymer to itself once it has been complexed with a polynucleic acid, or as a site of attachment for a second anionic layer when a cleavable polymer/polynucleic acid particle is being recharged to an anionic particle. An example of such a molecule is 3,3'-(N',N''-tert-butoxycarbonyl)-N-(3'-trifluoroacetamidylpropane)-N-methyldipropylammonium bromide (see experimental), this molecule would be incorporated by removing the two BOC protecting groups, incorporating the deprotected monomer into the bulk polymer, followed by deprotection of the trifluoroacetamide protecting group.

Cleavable Anionic Polymers

Cleavable anionic polymers can be designed in much the same manner as the cationic polymers. Short, multi-valent oligopeptides of glutamic or aspartic acid can be synthesized with the carboxy terminus capped with ethylene diamine. This oligo can the be incorporated into a bulk polymer as a co-monomer with any of the amine reactive disulfide containing crosslinkers mentioned previously. A preferred crosslinker would make use of NHS esters as the reactive group to avoid retention of positive charge as occurs with imidates. The cleavable anionic polymers can be used to recharge positively charged particles of condensed polynucleic acids.

Examples of cleavable polymers:

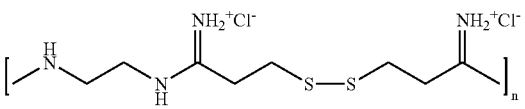

Co-ethylenediamine/DTBP cleavable cationic polymer

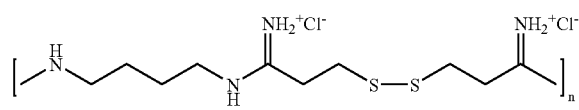

Co-diaminobutane/DTBP cleavable cationic polymer

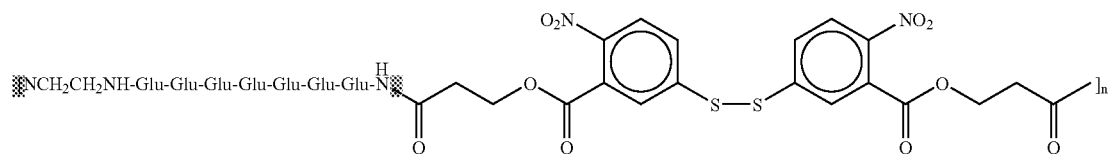

Co-glutamic acid/activated disulfide cleavable anionic polymer

The cleavable anionic polymers can have co-monomers incorporated to allow attachment of cell-specific ligands, endosome disrupting peptides, fluorescent marker molecules, as a site of attachment for further crosslinking of the polymer to itself once it has been complexed with a polynucleic acid, or as a site of attachment for to the initial cationic layer. For example the carboxyl groups on a portion of the anionic co-monomer could be coupled to an aminoalcohol such as 4-hydroxybutylamine. The resulting alcohol containing comonomer can be incorporated into the bulk polymer at any ratio. The alcohol functionalities can then be oxidized to aldehydes, which can be coupled to amine containing ligands etc. in the presence of sodium cyanoborohydride via reductive amination.

Synthesis of Activated Disulfide Containing Co-monomers

Synthesis of 5,5'-dithiobis(2-nitrobenzoate)propionitrile: 5,5'-dithiobis(2-nitrobenzoic acid) [Ellman's reagent] (500 mg, 1.26 mmol) was dissolved in 4.0 ml dioxane. Dicylohexylcarbodiimide (540 mg, 2.6 mmol) and 3-hydroxypropionitrile (240 μL, 188 mg, 2.60 mmol) were added. The reaction mixture was stirred overnight at room temperature. The urea precipitate was removed by centrifugation. The dioxane was removed on rotary evaporator. The residue was washed with saturated bicarbonate, water, and brine; and dried over magnesium sulfate. Solvent removal yielded 696 mg yellow/orange foam. The residue was purified using normal phase HPLC (Alltech econosil, 250×22 nm), flow rate=9.0 ml/min, mobile phase=1% ethanol in chloroform, retention time=13 min. Removal of solvent afforded 233 mg (36.8%) product as a yellow oil. TLC (silica: 5% methanol in chloroform; rf=0.51). $H^1$ NMR $\partial$ 8.05 (d, 4H), 7.75 (m, 4H), 4.55 (t, 4H), 2.85 (t, 4H).

Synthesis of 5,5'-dithiobis(2-nitrobenzoic acid)dimethyl propionimidate [DTNBP]: (113.5 mg, 0.226 mmol) was dissolved in 500 μL anhydrous chloroform along with anhydrous methanol (20.0 μL, 0.494 mmol). The flask was stoppered with a rubber septum, chilled to 0° C. on an ice bath, and HCl gas produced by mixing sulfuric acid and ammonium chloride was bubbled through the solution for a period of 10 minutes. The flask was then tightly sealed with parafilm and placed in a −20° C. freezer for a period of 48 hours. During this time a yellow oil formed. The oil was washed thoroughly with chloroform and dried under vacuum to yield 137 mg (95.8%) product as a yellow foam.

Compound 1

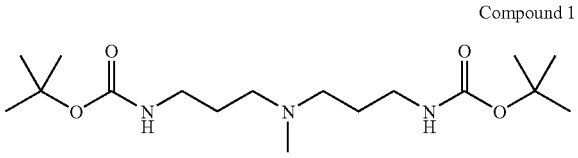

3,3'-(N,N''-tert-butoxycarbonyl)-N-methyldipropylamine (1). 3,3'-Diamino-N-methyldipropylamine (0.800 ml, 0.721 g, 5.0 mmol) was dissolved in 5.0 ml 2.2 N sodium hydroxide (11 mmol). To the solution was added Boc anhydride (2.50 ml, 2.38 g, 10.9 mmol) with magnetic stirring. The reaction mixture was allowed to stir at room temperature overnight (approximately 18 hours). The reaction mixture was made basic by adding additional 2.2 N NaOH until all t-butyl carboxylic acid was in solution. The solution was then extracted into chloroform (2×20 ml). The combined chloroform extracts were washed 2×10 ml water and dried over magnesium sulfate. Solvent removal yielded 1.01 g (61.7%) product as a white solid: $^1$H-NMR (CDCl$_3$) δ5.35 (bs, 2H), 3.17 (dt, 4H), 2.37 (t, 4H), 2.15 (s, 3H), 1.65 (tt, 4H), 1.45 (s, 18H).

Compound 13

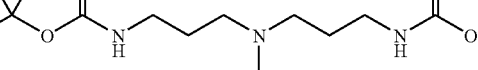

3,3'-(N',N''-tert-butoxycarbonyl)-N-(3'-trifluoroacetamidylpropane)-N-methyldipropylammonium bromide (13). Compound 1 (100.6 mg, 0.291 mmol) and compound 4 (76.8 mg, 0.328 mmol) were dissolved in 0.150 ml dimethylformamide. The reaction mixture was incubated at 50° C. for 3 days. TLC (reverse phase; acetonitrile: 50 mM ammonium acetate pH 4.0; 3:1) showed 1 major and 2 minor spots none of which corresponded to starting material. Recrystalization attempts were unsuccessful so product was precipitated from ethanol with ether yielding 165.5 mg (98.2%) product and minor impurities as a clear oil: $^1$H-NMR (CDCl$_3$) δ9.12 (bs,1H), 5.65 (bs, 2H), 3.50 (m, 8H), 3.20 (m, 4H), 3.15 (s, 3H), 2.20 (m, 2H), 2.00 (m, 4H), 1.45 (s, 18H).

Intravascular Injections of DNA/Polymer Complexes

Synthesis of N,N'-Bis(t-BOC)-L-cystine:

To a solution of L-cystine (1 μm, 4.2 mmol, Aldrich Chemical Company) in acetone (10 ml) and water (10 ml) was added 2-(tert-butoxycarbonyloxyimino)-2-phenylacetonitrile (2.5 gm, 10 mmol, Aldrich Chemical Company) and triethylamine (1.4 ml, 10 mmol, Aldrich Chemical Company). The reaction was allowed to stir overnight at room temperature. The water and acetone was then by rotary evaporation resulting in a yellow solid. The diBOC compound was then isolated by flash chromatography on silica gel eluting with ethyl acetate 0.1% acetic acid.

Synthesis of L-cystine—1,4-bis(3-aminopropyl)piperazine copolymer (M66):

To a solution of N,N'-Bis(t-BOC)-L-cystine (85 mg, 0.15 mmol) in ethyl acetate (20 ml) was added N,N'-dicyclohexylcarbodiimide (108 mg, 0.5 mmol) and N-hyroxysuccinimide (60 mg, 0.5 mmol). After 2 hr, the solution was filtered through a cotton plug and 1,4-bis(3-aminopropyl)piperazine (54 µL, 0.25 mmol) was added. The reaction was allowed to stir at room temperature for 16 h. The ethyl acetate was then removed by rotary evaporation and the resulting solid was dissolved in trifluoroacetic acid (9.5 ml), water (0.5 ml) and triisopropylsilane (0.5 ml). After 2 h, the trifluoroacetic acid was removed by rotary evaporation and the aqueous solution was dialyzed in a 15,000 MW cutoff tubing against water (2×2 l) for 24 h. The solution was then removed from dialysis tubing, filtered through 5 µM nylon syringe filter and then dried by lyophilization to yield 30 mg of polymer.

Injection of plasmid DNA (pCILuc)/L-cystine—1,4-bis (3-aminopropyl)piperazine copolymer (M66) complexes into the iliac artery of rats.

Complex formation—500 ug pDNA (500 ul) was mixed with M66 copolymer at a 1:3 wt:wt ratio in 500 ul saline. Complexes were then diluted in Ringers solution to total volume of 10 mls.

Injections—total volume of 10 mls was injected into the iliac artery of Sprague-Dawley rats (Harlan, Indianapolis, Ind.) in approximately 10 seconds.

Expression—Animals were sacrificed after 1 week and individual muscle groups were removed and assayed for luciferase expression.

Rat hind limb muscle groups.
1) upper leg posterior—$6.46\times10^8$ total Relative Light Units (32 ng luciferase)
2) upper leg anterior—$3.58\times10^9$ total Relative Light Units (183 ng luciferase)
3) upper leg middle—$2.63\times10^9$ total Relative Light Units (134 ng luciferase)
4) lower leg anterior—$3.19\times10^9$ total Relative Light Units (163 ng luciferase)
5) lower leg anterior—$1.97\times10^9$ total Relative Light Units (101 ng luciferase)

These results indicate that high level gene expression in all muscle groups of the leg was facilitated by intravascular delivery of pCILuc/M66 complexes into rat iliac artery.

Synthesis of 5,5'-Dithiobis[succinimidyl(2-nitrobenzoate):

5,5'-dithiobis(2-nitrobenzoic acid) (50.0 mg, 0.126 mmol, Aldrich Chemical Company) and N-hyroxysuccinimide (29.0 mg, 0.252 mmol, Aldrich Chemical Company) were taken up in 1.0 ml dichloromethane. Dicylohexylcarbodiimide (52.0 mg, 0.252 mmol) was added and the reaction mixture was stirred overnight at room temperature. After 16 hr, the reaction mixture was partitioned in EtOAc/$H_2O$. The organic layer was washed 2×$H_2O$, 1×brine, dried ($MgSO_4$) and concentrated under reduced pressure. The residue was taken up in $CH_2Cl_2$, filtered, and purified by flash column chromatography on silica gel (130×30 mm, EtOAc:$CH_2Cl_2$ 1:9 eluent) to afford 42 mg (56%) 5,5'-dithiobis[succinimidyl(2-nitrobenzoate)] as a white solid. $H^1$ NMR (DMSO) $\partial$ 7.81 7.77 (d, 2H), 7.57–7.26 (m, 4H), 3.69 (s, 8 H).

Synthesis of 5,5'-Dithiobis(2-nitrobenzoic acid)-Pentaethylenehexamine Copolymer (M72):

Pentaethylenehexamine (4.2 µL, 0.017 mmol, Aldrich Chemical Company) was taken up in 1.0 ml dichloromethane and HCl (1 ml, 1 M in $Et_2O$, Aldrich Chemical Company) was added $Et_2O$ was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropylethylamine (12 µL, 0.068 mmol, Aldrich Chemical Company) was added dropwise. After 16 hr, the solution was cooled, diluted with 3 ml $H_2O$, and dialyzed in 12,000–14,000 MW cutoff tubing against water (2×2 L) for 24 hr. The solution was then removed from dialysis tubing and dried by lyophilization to yield 5.9 mg (58%) of 5,5'-dithiobis(2-nitrobenzoic acid)-pentaethylenehexamine Copolymer.

Synthesis of 5,5'-Dithiobis(2-nitrobenzoic acid)-Tetraethylenepentamine Copolymer (#M57):

Tetraethylenepentamine (3.2 µL, 0.017 mmol, Aldrich Chemical Company) was taken up in 1.0 ml dichloromethane and HCl (1 ml, 1 M in $Et_2O$, Aldrich Chemical Company) was added $Et_2O$ was added and the resulting HCl salt was collected by filtration. The salt was taken up in 1 ml DMF and 5,5'-dithiobis[succinimidyl (2-nitrobenzoate)] (10 mg, 0.017 mmol) was added. The resulting solution was heated to 80° C. and diisopropylethylamine (15 µL, 0.085 mmol, Aldrich Chemical Company) was added dropwise. After 16 hr, the solution was cooled, diluted with 3 ml $H_2O$, and dialyzed in 12,000–14,000 MW cutoff tubing against water (2×2 L) for 24 h. The solution was then removed from dialysis tubing and dried by lyophilization to yield 5.8 mg (62%) of 5,5'-dithiobis(2-nitrobenzoic acid)-tetraethylenepentamine copolymer.

Mouse Tail Vein Injections of pDNA (pCI Luc)/5,5'-Dithiobis(2-nitrobenzoic acid)-Tetraethylenepentamine Copolymer Complexes:

Complexes were prepared as follows:
Complex I: pDNA (pCI Luc, 200 µg) was added to 300 µL DMSO then 2.5 ml Ringers was added.
Complex II: pDNA (pCI Luc, 200 µg) was added to 300 µL DMSO then 5,5'-Dithiobis(2-nitrobenzoic acid)-Tetraethylenepentamine Copolymer (336 µg) was added followed by 2.5 ml Ringers.

High pressure (2.5 ml) tail vein injections of the complex were performed as previously described (Zhang, G., Budker, V., Wolff, J. "High Levels of Foreign Gene Expression in Hepatocytes from Tail Vein Injections of Naked Plasmid DNA", Human Gene Therapy, July, 1999). Results reported are for liver expression, and are the average of two mice. Luciferase expression was determined as previously reported (Wolff, J. A., Malone, R. W., Williams, P., Chong, W., Acsadi, G., Jani, A., and Felgner, P. L., 1990 "Direct gene transfer into mouse muscle in vivo," Science 247, 1465–8.) A Lumat LB 9507 (EG&G Berthold, Bad-Wildbad, Germany) luminometer was used.

Results: High pressure injections
Complex I: 25,200,000 Relative Light Units
Complex II: 21,000,000 Relative Light Units Results indicate that pDNA (pCI Luc)/5,5'-Dithiobis(2-nitrobenzoic acid)-tetraethylenepentamine copolymer complexes are nearly equivalent to pCI Luc DNA itself in high pressure injections. This indicates that the pDNA is being released from the complex and is accessible for transcription.

Synthesis of 5,5'-Dithiobis(2-nitrobenzoic acid)-Tetraethylenepentamine-Tris(2-aminoethyl)amine Copolymer (#M58):

Tetraethylenepentamine (2.3 µL, 0.012 mmol, Aldrich Chemical Company) and tris(2-aminoethyl)amine (0.51 µL, 0.0034 mmol, Aldrich Chemical Company) were taken up in 0.5 ml methanol and HCl (1 ml, 1 M in $Et_2O$, Aldrich Chemical Company) was added. $Et_2O$ was added and the resulting HCl salt was collected by filtration. The salt was taken up in 1 ml DMF and 5,5'-dithiobis[succinimidyl (2-nitrobenzoate)] (10 mg, 0.017 mmol) was added. The resulting solution was heated to 80° C. and diisopropylethylamine (15 µL, 0.085 mmol, Aldrich Chemical Company) was added dropwise. After 16 hr, the solution was cooled, diluted with 3 ml $H_2O$, and dialyzed in 12,000–14,000 MW cutoff tubing against water (2×2 L) for 24 h. The solution was then removed from dialysis tubing and dried by lyophilization to yield 6.9 mg (77%) of 5,5'-dithiobis(2-nitrobenzoic acid)-tetraethylenepentamine-tris(2-aminoethyl) amine copolymer.

Mouse Tail Vein Injections of pDNA (pCI Luc)/5,5'-Dithiobis(2-nitrobenzoic acid)-Tetraethylenepentamine-Tris(2-aminoethyl)amine Copolymer Complexes:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300 µL DMSO then 5,5'-Dithiobis(2-nitrobenzoic acid)-Tetraethylenepentamine-Tris(2-aminoethyl)amine Copolymer (324 µg) was added followed by 2.5 ml Ringers.

High pressure (2.5 ml) tail vein injections of the complex were performed as previously described. Results reported are for liver expression, and are the average of two mice. Luciferase expression was determined a previously shown.

Results: High pressure injections

Complex I: 25,200,000 Relative Light Units

Complex II: 37,200,000 Relative Light Units

Results indicate that pDNA (pCI Luc)/5,5'-Dithiobis(2-nitrobenzoic acid)-tetraethylenepentamine-Tris(2-aminoethyl)amine Copolymer Complexes are more effective than pCI Luc DNA in high pressure injections. This indicates that the pDNA is being released from the complex and is accessible for transcription.

Synthesis of 5,5'-Dithiobis(2-nitrobenzoic acid)-N,N'-Bis(2-aminoethyl)-1,3-propanediamine Copolymer (#M59):

N,N'-Bis(2-aminoethyl)-1,3-propanediamine (2.8 µL, 0.017 mmol, Aldrich Chemical Company) was taken up in 1.0 ml dichloromethane and HCl (1 ml, 1 M in $Et_2O$, Aldrich Chemical Company) was added. $Et_2O$ was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropylethylamine (12 µL, 0.068 mmol, Aldrich Chemical Company) was added dropwise. After 16 hr, the solution was cooled, diluted with 3 ml $H_2O$, and dialyzed in 12,000–14,000 MW cutoff tubing against water (2×2 L) for 24 hr. The solution was then removed from dialysis tubing and dried by lyophilization to yield 5.9 mg (66%) of 5,5'-dithiobis(2-nitrobenzoic acid)-N,N'-bis(2-aminoethyl)-1,3-propanediamine Copolymer.

Mouse Tail Vein Injections of pDNA (pCI Luc)/5,5'-Dithiobis(2-nitrobenzoic acid)—N,N'-Bis(2-aminoethyl)-1,3-propanediamine Copolymer Complexes:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300µL DMSO then 5,5'-Dithiobis(2-nitrobenzoic acid)-N,N'-Bis (2-aminoethyl)-1,3-propanediamine Copolymer (474 µg) was added followed by 2.5 ml Ringers.

High pressure tail vein injections of 2.5 ml of the complex were performed as previously described. Results reported are for liver expression, and are the average of two mice. Luciferase expression was determined as previously shown.

Results: High pressure injections

Complex I: 25,200,000 Relative Light Units

Complex II: 341,000 Relative Light Units

Results indicate that pDNA (pCI Luc)/5,5'-Dithiobis(2-nitrobenzoic acid)-tetraethylenepentamine Copolymer Complexes are less effective than pCI Luc DNA in high pressure injections. Although the complex was less effective, the luciferase expression indicates that the pDNA is being released from the complex and is accessible for transcription.

Synthesis of 5,5'-Dithiobis(2-nitrobenzoic acid)—N,N'-Bis(2-aminoethyl)-1,3-propanediamine-Tris(2-aminoethyl) amine Copolymer (#M60):

N,N'-Bis(2-aminoethyl)-1,3-propanediamine (2.0 µL, 0.012 mmol, Aldrich Chemical Company) and tris(2-aminoethyl)amine (0.51 µL, 0.0034 mmol, Aldrich Chemical Company) were taken up in 0.5 ml methanol and HCl (1 ml, 1 M in $Et_2O$, Aldrich Chemical Company) was added. $Et_2O$ was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropylethylamine (12 µL, 0.068 mmol, Aldrich Chemical Company) was added dropwise. After 16 hr, the solution was cooled, diluted with 3 ml $H_2O$, and dialyzed in 12,000–14,000 MW cutoff tubing against water (2×2 L) for 24 hr. The solution was then removed from dialysis tubing and dried by lyophilization to yield 6.0 mg (70%) of 5,5'-dithiobis(2-nitrobenzoic acid)—N,N'-bis(2-aminoethyl)-1,3-propanediamine—tris(2-aminoethyl)amine copolymer.

Mouse Tail Vein Injections of pDNA (pCI Luc)/5,5'-Dithiobis(2-nitrobenzoic acid)—N,N'-Bis(2-aminoethyl)-1,3-propanediamine-Tris(2-aminoethyl)amine Copolymer Complexes:

Complexes were prepared as follows:

Complex I: pDNA (pCI Luc, 200 µg) was added to 300 µL DMSO then 2.5 ml Ringers was added.

Complex II: pDNA (pCI Luc, 200 µg) was added to 300 µL DMSO then 5,5'-Dithiobis(2-nitrobenzoic acid)-N,N'-Bis (2-aminoethyl)-1,3-propanediamine-Tris(2-aminoethyl) amine Copolymer (474 µg) was added followed by 2.5 ml Ringers.

High pressure tail vein injections of 2.5 ml of the complex were preformed as previously described. Results reported are for liver expression, and are the average of two mice. Luciferase expression was determined as previously shown.

Results: High pressure injections

Complex I: 25,200,000 Relative Light Units

Complex II: 1,440,000 Relative Light Units

Results indicate that pDNA (pCI Luc)/5,5'-Dithiobis(2-nitrobenzoic acid)—N,N'-Bis(2-aminoethyl)-1,3-propanediamine—Tris(2-aminoethyl)amine Copolymer Complexes are less effective than pCI Luc DNA in high pressure injections. Although the complex was less effective, the luciferase expression indicates that the pDNA is being released from the complex and is accessible for transcription.

Synthesis of guanidino-L-cystine 1,4-bis(3-aminopropyl) piperazine Copolymer (#M67):

To a solution of cystine (1 gm, 4.2 mmol) in ammonium hydroxide (10 ml) in a screw-capped vial was added O-methylisourea hydrogen sulfate (1.8 gm, 10 mmol). The vial was sealed and heated to 60° C. for 16 h. The solution was then cooled and the ammonium hydroxide was removed by rotary evaporation. The solid was then dissolved in water (20 ml), filtered through a cotton plug. The product was then isolated by ion exchange chromatography using Bio-Rex 70 resin and eluting with hydrochloric acid (100 mM).

Synthesis of guanidino-L-cystine1,4-bis(3-aminopropyl) piperazine Copolymer:

To a solution of guanidino-L-cystine (64 mg, 0.2 mmol) in water (10 ml) was slowly added N,N'-dicyclohexylcarbodiimide (82 mg, 0.4 mmol) and N-hyroxysuccinimide (46 mg, 0.4 mmol) in dioxane (5 ml). After 16 hr, the solution was filtered through a cotton plug and 1,4-bis(3-aminopropyl)piperazine (40 µL, 0.2 mmol) was added. The reaction was allowed to stir at room temperature for 16 h and then the aqueous solution was dialyzed in a 15,000 MW cutoff tubing against water (2×2 l) for 24 h. The solution was then removed from dialysis tubing, filtered through 5 µM nylon syringe filter and then dried by lyophilization to yield 5 mg of polymer.

Particle Size of pDNA-L-cystine-1,4-bis(3-aminopropyl) piperazine Copolymer and DNA-guanidino-L-cystine1,4-bis(3-aminopropyl)piperazine Copolymer Complexes:

To a solution of pDNA (10 µg/ml) in 0.5 ml 25 mM HEPES buffer pH 7.5 was added 10 µg/ml L-cystine—1,4-bis(3-aminopropyl)piperazine copolymer or guanidino-L-cystine1,4-bis(3-aminopropyl)piperazine copolymer. The size of the complexes between DNA and the polymers were measured. For both polymers, the size of the particles were approximately 60 nm.

Condensation of DNA with L-cystine-1,4-bis(3-aminopropyl)piperazine Copolymer and Decondensation of DNA upon Addition of Glutathione:

Fluorescein labeled DNA was used for the determination of DNA condensation in complexes with L-cystine-1,4-bis(3-aminopropyl)piperazine copolymer. pDNA was modified to a level of 1 fluorescein per 100 bases using Mirus' LabelIT Fluorescein kit. The fluorescence was determined using a fluorescence spectrophotometer (Shimadzu RF-1501 spectrofluorometer) at an excitation wavelength of 495 nm and an emission wavelength of 530 nm (Trubetskoy, V. S., Slattum, P. M., Hagstrom, J. E., Wolff, J. A., and Budker, V. G., "Quantitative assessment of DNA condensation," Anal Biochem 267, 309–13 (1999), incorporated herein by reference).

The intensity of the fluorescence of the fluorescein-labeled DNA (10 µg/ml) in 0.5 ml of 25 mM HEPES buffer pH 7.5 was 300 units. Upon addition of 10 µg/ml of L-cystine-1,4-bis(3-aminopropyl)piperazine copolymer, the intensity decreased to 100 units. To this DNA-polycation sample was added 1 mM glutathione and the intensity of the fluorescence was measured. An increase in intensity was measured to the level observed for the DNA sample alone. The half life of this increase in fluorescence was 8 minutes.

The experiment indicates that DNA complexes with physiologically-labile disulfide-containing polymers are cleavable in the presence of the biological reductant glutathione.

Mouse Tail Vein Injection of DNA-L-cystine-1,4-bis(3-aminopropyl)piperazine Copolymer and DNA-guanidino-L-cystine1,4-bis(3-aminopropyl)piperazine Copolymer Complexes:

Plasmid delivery in the tail vein of ICR mice was performed as previously described. To pCILuc DNA (50 µg) in 2.5 ml H$_2$O was added either L-cystine-1,4-bis(3-aminopropyl)piperazine copolymer, guanidino-L-cystine1,4-bis(3-aminopropyl)piperazine copolymer, or poly-L-lysine (34,000 MW, Sigma Chemical Company) (50 µg). The samples were then injected into the tail vein of mice using a 30 gauge, 0.5 inch needle. One day after injection, the animal was sacrificed, and a luciferase assay was conducted.

| Polycation | ng/liver |
|---|---|
| poly-L-lysine | 6.2 |
| L-cystine-1,4-bis(3-aminopropyl)piperazine copolymer | 439 |
| guanidino-L-cystine1,4-bis(3-aminopropyl)piperazine copolymer | 487 |

The experiment indicates that DNA complexes with the physiologically-labile disulfide-containing polymers are capable of being broken, thereby allowing the luciferase gene to be expressed.

Synthesis of 5,5'-Dithiobis(2-nitrobenzoic acid)-Pentaethylenehexamine Copolymer (#M69):

Pentaethylenehexamine (4.2 µL, 0.017 mmol, Aldrich Chemical Company) was taken up in 1.0 ml dichloromethane and HCl (1 ml, 1 M in Et$_2$O, Aldrich Chemical Company) was added Et$_2$O was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropylethylamine (12 µL, 0.068 mmol, Aldrich Chemical Company) was added dropwise. After 16 hr, the solution was cooled, diluted with 3 ml H$_2$O, and dialyzed in 12,000–14,000 MW cutoff tubing against water (2×2 L) for 24 hr. The solution was then removed from dialysis tubing and dried by lyophilization to yield 5.9 mg (58%) of 5,5'-dithiobis(2-nitrobenzoic acid)-pentaethylenehexamine Copolymer.

Synthesis of 5,5'-Dithiobis(2-nitrobenzoic acid)-Pentaethylenehexamine-Tris(2-aminoethyl)amine Copolymer (#M70):

Pentaethylenehexamine (2.9 µL, 0.012 mmol, Aldrich Chemical Company) and tris(2-aminoethyl)amine (0.51 µL, 0.0034 mmol, Aldrich Chemical Company) were taken up in 0.5 ml methanol and HCl (1 ml, 1 M in Et$_2$O, Aldrich Chemical Company) was added. Et$_2$O was added and the resulting HCl salt was collected by filtration. The salt was taken up in 1 ml DMF and 5,5'-dithiobis[succinimidyl(2-nitrobenzoate)] (10 mg, 0.017 mmol) was added. The resulting solution was heated to 80° C. and diisopropylethylamine (12 µL, 0.068 mmol, Aldrich Chemical Company) was added dropwise. After 16 hr, the solution was cooled, diluted with 3 ml H$_2$O, and dialyzed in 12,000–14,000 MW cutoff tubing against water (2×2 L) for 24 h. The solution was then removed from dialysis tubing and dried by lyophilization to yield 6.0 mg (64%) of 5,5'-dithiobis(2-nitrobenzoic acid)-pentaethylenehexamine-tris(2-aminoethyl)amine copolymer.

pH Cleavable Polymers for Intracellular Compartment Release

A cellular transport step that has importance for gene transfer and drug delivery is that of release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Chemicals such as chloroquine, bafilomycin or Brefeldin A1. Chloroquine decreases the acidification of the endosomal and lysosomal compartments but also affects other cellular functions. Brefeldin A, an isoprenoid fungal metabolite, collapses reversibly the Golgi apparatus into the endoplasmic reticulum and the early endosomal compartment into the trans-Golgi network (TGN) to form tubules. Bafilomycin $A_1$, a macrolide antibiotic is a more specific inhibitor of endosomal acidification and vacuolar type $H^+$-ATPase than chloroquine. The ER-retaining signal (KDEL sequence) has been proposed to enhance delivery to the endoplasmic reticulum and prevent delivery to lysosomes.

To increase the stability of DNA particles in serum, we have added to positively-charged DNA-polycation particles polyanions that form a third layer in the DNA complex and make the particle negatively charged. To assist in the disruption of the DNA complexes, we have synthesized polymers that are cleaved in the acid conditions found in the endosome, pH 5–7. We also have reason to believe that cleavage of polymers in the DNA complexes in the endosome assists in endosome disruption and release of DNA into the cytoplasm.

There are two ways to cleave a polyion: cleavage of the polymer backbone resulting in smaller polyions or cleavage of the link between the polymer backbone and the ion resulting in an ion and an polymer. In either case, the interaction between the polyion and DNA is broken and the number of molecules in the endosome increases. This causes an osmotic shock to the endosomes and disrupts the endosomes. In the second case, if the polymer backbone is hydrophobic it may interact with the membrane of the endosome. Either effect may disrupt the endosome and thereby assist in release of DNA.

To construct cleavable polymers, one may attach the ions or polyions together with bonds that are inherently labile such as disulfide bonds, diols, diazo bonds, ester bonds, sulfone bonds, acetals, ketals, enol ethers, enol esters, imines, imminiums, and enamines. Another approach is construct the polymer in such a way as to put reactive groups, i.e. electrophiles and nucleophiles, in close proximity so that reaction between the function groups is rapid. Examples include having carboxylic acid derivatives (acids, esters, amides) and alcohols, thiols, carboxylic acids or amines in the same molecule reacting together to make esters, thiol esters, acid anhydrides or amides.

In one embodiment, ester acids and amide acids that are labile in acidic environments (pH less than 7, greater than 4) to form an alcohol and amine and an anhydride are use in a variety of molecules and polymers that include peptides, lipids, and liposomes.

In one embodiment, ketals that are labile in acidic environments (pH less than 7, greater than 4) to form a diol and a ketone are use in a variety of molecules and polymers that include peptides, lipids, and liposomes.

In one embodiment, acetals that are labile in acidic environments (pH less than 7, greater than 4) to form a diol and an aldehyde are use in a variety of molecules and polymers that include peptides, lipids, and liposomes.

In one embodiment, enols that are labile in acidic environments (pH less than 7, greater than 4) to form a ketone and an alcohol are use in a variety of molecules and polymers that include peptides, lipids, and liposomes.

In one embodiment, iminiums that are labile in acidic environments (pH less than 7, greater than 4) to form an amine and an aldehyde or a ketone are use in a variety of molecules and polymers that include peptides, lipids, and liposomes.

pH-Sensitive Cleavage of Peptides and Polypeptides

In one embodiment, peptides and polypeptides (both referred to as peptides) are modified by an anhydride. The amine (lysine), alcohol (serine, threonine, tyrosine), and thiol (cysteine) groups of the peptides are modified by the an anhydride to produce an amide, ester or thioester acid. In the acidic environment of the internal vesicles (pH less than 6.5, greater than 4.5) (early endosomes, late endosomes, or lysosome) the amide, ester, or thioester is cleaved displaying the original amine, alcohol, or thiol group and the anhydride.

A variety of endosomolytic and amphipathic peptides can be used in this embodiment. A positively-charged amphipathic/endosomolytic peptide is converted to a negatively-charged peptide by reaction with the anhydrides to form the amide acids and this compound is then complexed with a polycation-condensed nucleic acid. After entry into the endosomes, the amide acid is cleaved and the peptide becomes positively charged and is no longer complexed with the polycation-condensed nucleic acid and becomes amphipathic and endosomolytic. In one embodiment the peptides contains tyrosines and lysines. In yet another embodiment, the hydrophobic part of the peptide (after cleavage of the ester acid) is at one end of the peptide and the hydrophilic part (e.g. negatively charged after cleavage) is at another end. The hydrophobic part could be modified with a dimethylmaleic anhydride and the hydrophilic part could be modified with a citranconyl anhydride. Since the dimethylmaleyl group is cleaved more rapidly than the citrconyl group, the hydrophobic part forms first. In another embodiment the hydrophilic part forms alpha helixes or coil-coil structures.

pH-Sensitive Cleavage of Lipids and Liposomes

In another embodiment, the ester, amide or thioester acid is complexed with lipids and liposomes so that in acidic environments the lipids are modified and the liposome becomes disrupted, fusogenic or endosomolytic. The lipid diacylglycerol is reacted with an anhydride to form an ester acid. After acidification in an intracellular vesicle the diacylglycerol reforms and is very lipid bilayer disruptive and fusogenic.

Synthesis of Citraconylpolyvinylphenol

Polyvinylphenol (10 mg 30,000 MW Aldrich Chemical) was dissolved in 1 ml anhydrous pyridine. To this solution was added citraconic anhydride (100 μL, 1 mmol) and the solution was allowed to react for 16 hr. The solution was then dissolved in 5 ml of aqueous potassium carbonate (100 mM) and dialyzed three times against 2 L water that was at pH8 with addition of potassium carbonate. The solution was then concentrated by lyophilization to 10 mg/ml of citraconylpolyvinylphenol.

Synthesis of citraconylpoly-L-tyrosine

Poly-L-tyrosine (10 mg, 40,000 MW Sigma Chemical) was dissolved in 1 ml anhydrous pyridine. To this solution was added citraconic anhydride (100 μL, 1 mmol) and the solution was allowed to react for 16 hr. The solution was then dissolved in 5 ml of aqueous potassium carbonate (100 mM) and dialyzed against 3×2 L water that was at pH8 with addition of potassium carbonate. The solution was then concentrated by lyophilization to 10 mg/ml of citraconylpoly-L-tyrosine.

Synthesis of citraconylpoly-L-lysine

Poly-L-lysine (10 mg 34,000 MW Sigma Chemical) was dissolved in 1 ml of aqueous potassium carbonate (100 mM). To this solution was added citraconic anhydride (100 μL, 1 mmol) and the solution was allowed to react for 2 hr. The solution was then dissolved in 5 ml of aqueous potassium carbonate (100 mM) and dialyzed against 3×2 L water that was at pH8 with addition of potassium carbonate. The solution was then concentrated by lyophilization to 10 mg/ml of citraconylpoly-L-lysine.

Synthesis of dimethylmaleylpoly-L-lysine

Poly-L-lysine (10 mg 34,000 MW Sigma Chemical) was dissolved in 1 ml of aqueous potassium carbonate (100 mM). To this solution was added 2,3-dimethylmaleic anhydride (100 mg, 1 mmol) and the solution was allowed to react for 2 hr. The solution was then dissolved in 5 ml of aqueous potassium carbonate (100 mM) and dialyzed against 3×2 L water that was at pH8 with addition of potassium carbonate. The solution was then concentrated by lyophilization to 10 mg/ml of dimethylmaleylpoly-L-lysine.

Characterization of Particles Formed with Citraconylated and Dimethylmaleylated Polymers To a complex of DNA (20 μg/ml) and poly-L-lysine (40 μg/ml) in 1.5 ml was added the various citraconylpolyvinylphenol and citraconylpoly-L-lysine (150 μg/ml). The sizes of the particles formed were measured to be 90–120 nm and the zeta potentials of the particles were measured to be −10 to −30 mV (Brookhaven ZetaPlus Particle Sizer).

To each sample was added acetic acid to make the pH 5. The size of the particles was measured as a function of time. Both citraconylpolyvinylphenol and citraconylpoly-L-lysine DNA complexes were unstable under acid pH. The citraconylpolyvinylphenol sample had particles>1 μm in 5 minutes and citraconylpoly-L-lysine sample had particles>1 μm in 30 minutes.

Synthesis of Glutaric Dialdehyde-Poly-Glutamic acid (8 mer) Copolymer $H_2N$-EEEEEEEE-$NHCH_2CH_2NH_2$ (5.5 mg, 0.0057 mmol, Genosys) was taken up in 0.4 ml $H_2O$. Glutaric dialdehyde (0.52 μL, 0.0057 mmol, Aldrich Chemical Company) was added and the mixture was stirred at room temperature. After 10 min the solution was heated to 70° C. After 15 hrs, the solution was cooled to room temperature and dialyzed against $H_2O$ (2×2L, 3500 MWCO). Lyophilization afforded 4.3 mg (73%) glutaric dialdehyde-polyglutamic acid (8 mer) copolymer.

Synthesis of Ketal from Polyvinylphenyl Ketone and Glycerol

Polyvinyl phenyl ketone (500 mg, 3.78 mmol, Aldrich Chemical Company) was taken up in 20 ml dichloromethane. Glycerol (304 μL, 4.16 mmol, Acros Chemical Company) was added followed by p-toluenesulfonic acid monohydrate (108 mg, 0.57 mmol, Aldrich Chemical Company). Dioxane (10 ml) was added and the solution was stirred at room temperature overnight. After 16 hrs, TLC indicated the presence of ketone. The solution was concentrated under reduced pressure, and the residue redissolved in DMF (7 ml). The solution was heated to 60° C. for 16 hrs. Dialysis against $H_2O$ (1×3L, 3500 MWCO), followed by Lyophilization resulted in 606 mg (78%) of the ketal.

Synthesis of Ketal Acid of Polyvinylphenyl Ketone and Glycerol Ketal

The ketal from polyvinylphenyl ketone and glycerol (220 mg, 1.07 mmol) was taken up in dichloromethane (5 ml). Succinic anhydride (161 mg, 1.6 mmol, Sigma Chemical Company) was added followed by diisopropylethyl amine (0.37 ml, 2.1 mmol, Aldrich Chemical Company) and the solution was heated at reflux. After 16 hrs, the solution was concentrated, dialyzed against $H_2O$ (1×3L, 3500 MWCO), and lyophilized to afford 250 mg (75%) of the ketal acid.

Particle Sizing and Acid Lability of Poly-L-Lysine/Ketal Acid of Polyvinylphenyl Ketone and Glycerol Ketal Complexes Particle sizing (Brookhaven Instruments Corporation, ZetaPlus Particle Sizer, I90, 532 nm) indicated an effective diameter of 172 nm (40 μg) for the ketal acid Addition of acetic acid to a pH of 5 followed by particle sizing indicated a increase in particle size to 84000. A poly-L-lysine/ketal acid (40 μg, 1:3 charge ratio) sample indicated a particle size of 142 nm. Addition of acetic acid (5 μL, 6 N) followed by mixing and particle sizing indicated an effective diameter of 1970 nm. This solution was heated at 40° C. particle sizing indicated a effective diameter of 74000 and a decrease in particle counts.

Results:

The particle sizer data indicates the loss of particles upon the addition of acetic acid to the mixture.

Synthesis of Ketal from Polyvinyl Alcohol and 4-Acetylbutyric Acid

Polyvinylalcohol (200 mg, 4.54 mmol, 30,000–60,000 MW, Aldrich Chemical Company) was taken up in dioxane (10 ml). 4-acetylbutyric acid (271 μL, 2.27 mmol, Aldrich Chemical Company) was added followed by p-toluenesulfonic acid monohydrate (86 mg, 0.45 mmol, Aldrich Chemical Company). After 16 hrs, TLC indicated the presence of ketone. The solution was concentrated under reduced pressure, and the residue redissolved in DMF (7 ml). The solution was heated to 60° C. for 16 hrs. Dialysis against $H_2O$ (1×4L, 3500 MWCO), followed by lyophilization resulted in 145 mg (32%) of the ketal.

Particle Sizing and Acid Lability of Poly-L-Lysine/Ketal from Polyvinyl Alcohol and 4-Acetylbutyric Acid Complexes Particle sizing (Brookhaven Instruments Corporation, ZetaPlus Particle Sizer, I90, 532 nm) indicated an effective diameter of 280 nm (743 kcps) for poly-L-lysine/ketal from polyvinyl alcohol and 4-acetylbutyric acid complexes (1:3 charge ratio). A poly-L-lysine sample indicated no particle formation. Similarly, a ketal from polyvinyl alcohol and 4-acetylbutyric acid sample indicated no particle formation.

Acetic acid was added to the poly-L-lysine/ketal from polyvinyl alcohol and 4-acetylbutyric acid complexes to a pH of 4.5. Particle sizing indicated particles of 100 nm, but at a minimal count rate (9.2 kcps)

Results:

The particle sizer data indicates the loss of particles upon the addition of acetic acid to the mixture.

Synthesis of 1,4-Bis(3-aminopropyl)piperazine Glutaric Dialdehyde Copolymer 1,4-Bis(3-aminopropyl)piperazine (206 μL, 0.998 mmol, Aldrich Chemical Company) was taken up in 5.0 ml $H_2O$. Glutaric dialdehyde was (206 μL, 0.998 mmol, Aldrich Chemical Company) was added and the solution was stirred at room temperature. After 30 min, an additional portion of $H_2O$ was added (20 ml), and the mixture neutralized with 6 N HCl to pH 7, resulting in a red solution. Dialysis against $H_2O$ (3×3L, 12,000–14,000 MW cutoff tubing) and lyophilization afforded 38 mg (14%) of the copolymer Particle Sizing and Acid Lability of pDNA (pCI Luc)/1,4-Bis(3-aminopropyl)piperazine Glutaric Dialdehyde Copolymer Complexes (#M140)

To 50 μg pDNA in 2 ml HEPES (25 mM, pH 7.8) was added 135 μg 1,4-bis(3-aminopropyl)piperazine glutaric dialdehyde copolymer. Particle sizing (Brookhaven Instruments Corporation, ZetaPlus Particle Sizer, I90, 532 nm) indicated an effective diameter of 110 nm for the complex. A 50 μg pDNA in 2 ml HEPES (25 mM, pH 7.8) sample indicated no particle formation. Similarly, a 135 μg 1,4-bis (3-aminopropyl)piperazine glutaric dialdehyde copolymer in 2 ml HEPES (25 mM, pH 7.8) sample indicated no particle formation.

Acetic acid was added to the pDNA (pCI Luc)/1,4-bis(3-aminopropyl)piperazine glutaric dialdehyde copolymer complexes to a pH of 4.5. Particle sizing indicated particles of 2888 nm, and aggregation was observed.

Results:

1,4-Bis(3-aminopropyl)piperazine-glutaric dialdehyde copolymer condenses pDNA, forming small particles. Upon acidification, the particle size increases, and aggregation occurs, indicating cleavage of the polymeric immine.

Mouse Tail Vein Injections of pDNA (pCILuc)/1,4-Bis(3-aminopropyl)piperazine Glutaric Dialdehyde Copolymer Complexes Four complexes were prepared as follows:

Complex I: pDNA (pCI Luc, 50 μg) in 12.5 ml Ringers.

Complex II: pDNA (pCI Luc, 50 μg) was mixed with 1,4-bis(3-aminopropyl)piperazine glutaric dialdehyde copolymer (50 μg) in 1.25 ml HEPES 25 mM, pH 8. This solution was then added to 11.25 ml Ringers.

Complex III: pDNA (pCI Luc, 50 μg) was mixed with poly-L-lysine (94.5 μg, MW 42,000, Sigma Chemical Company) in 12.5 ml Ringers.

2.5 ml tail vein injections of 2.5 ml of the complex were preformed as previously described. Luciferase expression was determined as previously indicated.

Results: 2.5 ml injections

Complex I: 3,692,000 Relative Light Units

Complex II: 1,047,000 Relative Light Units

Complex III: 4,379 Relative Light Units

Results indicate an increased level of pCI Luc DNA expression in pDNA/1,4-bis(3-aminopropyl)piperazine glutaric dialdehyde copolymer complexes over pCI Luc DNA/poly-L-lysine complexes. These results also indicate that the pDNA is being released from the pDNA/1,4-Bis(3-aminopropyl)piperazine-glutaric dialdehyde copolymer complexes, and is accessible for transcription.

Non-Cleavable Polymers

Many cationic polymers such as histone (H1, H2a, H2b, H3, H4, H5), HMG proteins, poly-L-lysine, polyethylenimine, protamine, and poly-histidine are used to compact polynucleic acids to help facilitate gene delivery in vitro and in vivo. A key for efficient gene delivery using prior art methods is that the non-cleavable cationic polymers (both in vitro and in vivo) must be present in a charge excess over the DNA so that the overall net charge of the DNA/polycation complex is positive. Conversely, using our tail vein injection process having non-cleavable cationic polymer/DNA complexes we found that gene expression is most efficient when the overall net charge of the complexes are negative (DNA negative charge>polycation positive charge). Tail vein injections using cationic polymers commonly used for DNA condensation and in vitro gene delivery revealed that high gene expression occurred when the net charge of the complexes were negative.

Figure 3:
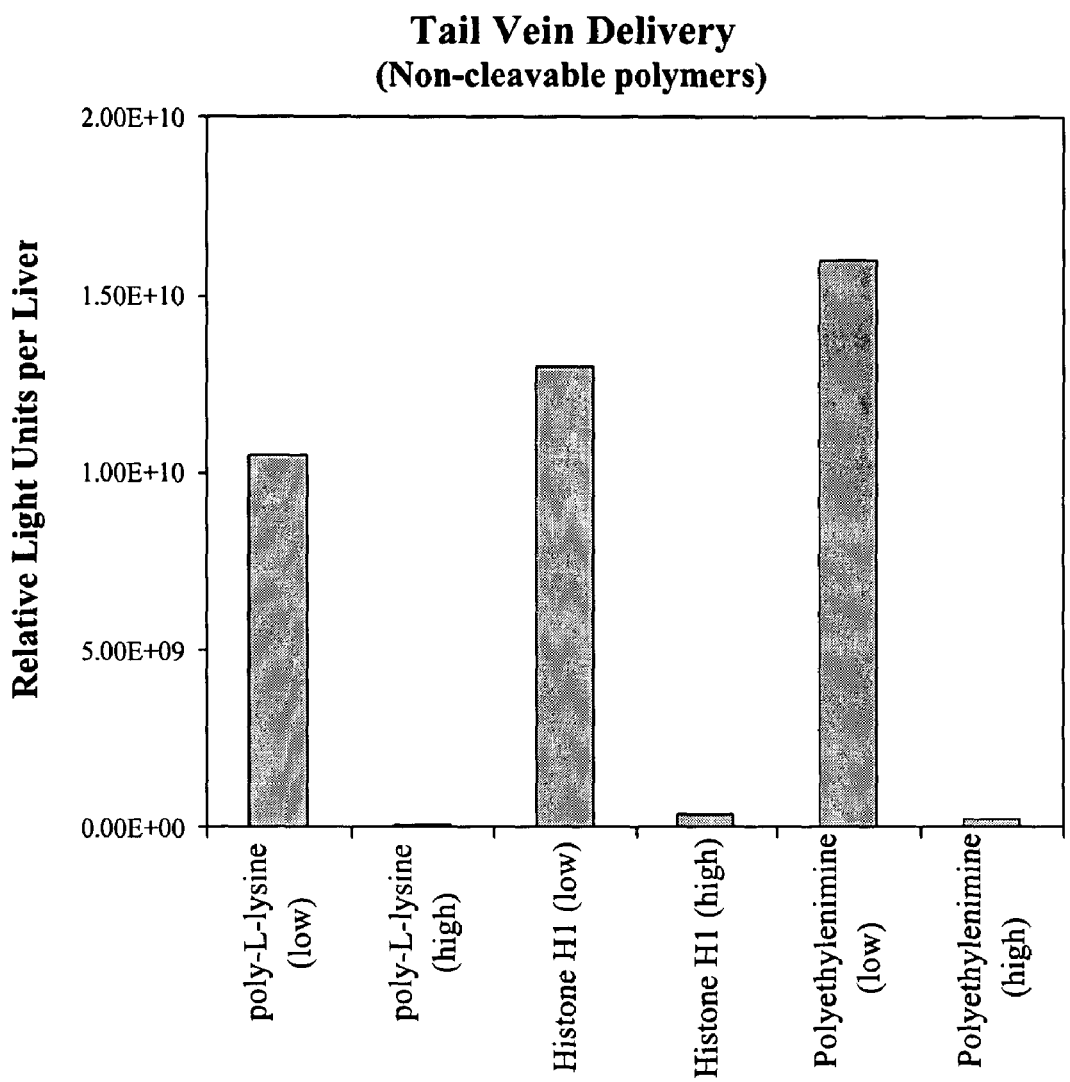
FIG. 3 illustrates Tail vein injection of pCILuc/polycation complexes in 2.5 ml ringers solution into 25 gram mice.

FIG. 3 illustrates tail vein injections of pCILuc/polycation complexes in 2.5 ml ringers solution into 25 gram mice as previously described (Zhang et al. Hum Gen Ther 10:1735, 1999). The low ratio of each polycation corresponds to wt:wt ratio of 0.5 polycation:1 DNA (net negative complex). The high ratio of each polycation corresponds to wt:wt ratio of 5 polycation:1 DNA (net positive complex).

High Efficiency Gene Expression Following Tail Vein Delivery of pDNA/Cationic Peptide Complexes Plasmid DNA (pCILuc) was mixed with an amphipathic cationic peptide at a 1:2 ratio (charge ratio) and diluted into 2.5 ml of Ringers solution per mouse. Complexes were injected into the tail vein of a 25 g ICR mouse (Harlan Sprague Dawley, Indianapolis, Ind.) in 7 seconds. Animals were sacrificed after 24 hours and livers were removed and assayed for luciferase expression.

Complex Preparation (per Mouse)

Complex I: pDNA (pCI Luc, 10 μg) in 2.5 ml Ringers.

Complex II: pDNA (pCI Luc, 10 μg) was mixed with cationic peptide (18 mer SEQ ID NO: 1 at a 1:2 ratio. Complexes were diluted to 2.5 ml with Ringers solution.

Tail vein injections of 2.5 ml of the complex were preformed as previously described.

Luciferase expression was determined as previously shown.

Results: 2.5 ml injections

Complex I: $1.63 \times 10^{10}$ Relative Light Units per liver

Complex II: $2.05 \times 10^{10}$ Relative Light Units per liver

The foregoing is considered as illustrative only of the principles of the invention. Furthermore, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering a naked non-expressed double strand RNA to an extravascular cell of a mammal, comprising: a) injecting the naked non-expressed double strand RNA into a blood vessel lumen, in vivo; b) increasing the propensity for macromolecules to move through vessel walls and enter the extravascular space; and, c) delivering the naked non-expressed double strand RNA to the extravascular cell outside of the blood vessel.

2. The process of claim 1 wherein the double strand RNA consists of an oligonucleotide of 120 or fewer bases.

3. The process of claim 1 wherein the double strand RNA consists of a polynucleotide of more than 120 bases.

4. The process of claim 1 wherein the non-expressed double strand RNA comprises a sequence that is similar to a gene sequence that is expressed.

5. The process of claim 1 wherein the nucleic acid consists of anti-sense non expressed double strand RNA.

6. The process of claim 1 wherein the propensity for macromolecules to move trough vessel walls and enter the extravascular space is increased by inserting papaverine into the vessel with the naked non-expressed double strand RNA.

7. The process of claim 1 wherein delivery of the naked non-expressed double strand RNA results in decreased expression of a gene.

8. The process of claim 7 wherein the gene is an endogenous gene.

9. The process of claim 7 wherein the gene is a viral gene.

10. The process of claim 1 wherein the vessel consists of a tail vein.

11. The process of claim 1 wherein the parenchymal cell is selected from the group consisting of liver cells, spleen cells, heart cells, kidney cells, prostate cells, skin cells, testis cells, skeletal muscle cells, fat cells, bladder cells, brain cells, pancreas cells, thymus cells, and lung cells.

12. A process for delivering a naked non-expressed double strand RNA to an extravascular cell of a mammal, comprising: injecting the naked nucleic acid into a tail vein, increasing pressure inside the tail vein and delivering the naked nucleic acid to an extravascular cell not within the tail.

13. The process of claim 12 wherein the parenchymal cell is a cell selected from the group consisting of liver cells, spleen cells, heart cells, kidney cells, prostate cells, skin cells, testis cells, skeletal muscle cells, fat cells, bladder cells, brain cells, pancreas cells, thymus cells, and lung cells.

14. The process of claim 12 wherein the double strand RNA comprises sequence that is similar to an expressed gene sequence.

* * * * *